United States Patent [19]
Anderson

[11] Patent Number: 5,261,766
[45] Date of Patent: Nov. 16, 1993

[54] VERTICAL BORE HOLE SYSTEM AND METHOD FOR WASTE STORAGE AND ENERGY RECOVERY

[76] Inventor: James S. Anderson, 62 Motherwell Crescent, Regina, Saskatchewan, Canada, S4S 3Z4

[21] Appl. No.: 912,483

[22] Filed: Jul. 13, 1992

[30] Foreign Application Priority Data

Sep. 6, 1991 [CA] Canada .................................. 2050777

Related U.S. Application Data

[63] Continuation-in-part of Ser. No. 757,048, Sep. 9, 1991, abandoned.

[51] Int. Cl.5 ................................................ B09B 3/00
[52] U.S. Cl. .................................... 405/129; 405/133; 405/150.1; 405/270
[58] Field of Search ................ 405/55, 128, 129, 133, 405/150.1, 270

[56] References Cited

U.S. PATENT DOCUMENTS

| | | |
|---|---|---|
| 2,164,536 | 7/1936 | McCarthy . |
| 3,415,022 | 12/1968 | Schaefer et al. ................ 405/220 |
| 3,545,213 | 12/1970 | Seber et al. ................ 405/150.1 X |
| 3,675,428 | 7/1972 | Watts . |
| 3,835,652 | 9/1974 | Hignite . |
| 4,026,355 | 5/1977 | Johnson et al. ................ 166/246 |
| 4,067,675 | 1/1978 | Hanson ................ 405/133 X |
| 4,191,492 | 3/1980 | Cobbs ................ 405/133 |
| 4,323,367 | 4/1982 | Ghosh . |
| 4,401,397 | 8/1983 | Sommer et al. ................ 405/133 |
| 4,469,176 | 9/1984 | Zison et al. . |
| 4,473,322 | 9/1984 | Echols et al. ................ 405/133 |
| 4,518,399 | 5/1985 | Croskell et al. . |
| 4,643,111 | 2/1987 | Jones . |
| 4,705,429 | 11/1987 | Natale . |
| 4,877,353 | 10/1989 | Wisotsky . |
| 5,000,617 | 3/1991 | Eggert et al. . |
| 5,000,618 | 3/1991 | Greenley . |

FOREIGN PATENT DOCUMENTS

| | | | |
|---|---|---|---|
| 1188525 | 6/1985 | Canada . | |
| 1253702 | 5/1989 | Canada . | |
| 204895 | 12/1986 | European Pat. Off. | ............ 405/128 |
| 278557 | 8/1988 | European Pat. Off. . | |
| 294656 | 12/1988 | European Pat. Off. . | |
| 85414 | 5/1982 | Japan | .................... 405/128 |
| 112908 | 6/1985 | Japan . | |
| 1211414 | 2/1986 | U.S.S.R. | ................ 405/270 |

Primary Examiner—Dennis L. Taylor
Assistant Examiner—Arlen L. Olsen
Attorney, Agent, or Firm—Robert W. B. Bailey

[57] ABSTRACT

Vertical bore holes are constructed for municipal sanitary landfills by drilling or otherwise excavating holes of large dimension to substantial depth, in virtually all known soil conditions however variable. They can be excavated well below the groundwater table, then lined with an impermeable or other permanent liner. This allows the landfill area to be much more efficiently used for the storage of various waste products. Solid organic waste other than cellulosics can be anaerobically fermented to methane and compost. A central core shaft is used as gas removal vent and conduit. After methane generation and removal the resulting compost is removed for use as soil nutrients. This system fully complies with the Environmental Protection Act and other regulations now in force in North America. Air, soil, groundwater, and surface water pollution and contamination are eliminated as all waste storage is contained within its own environment below natural grade.

18 Claims, 7 Drawing Sheets

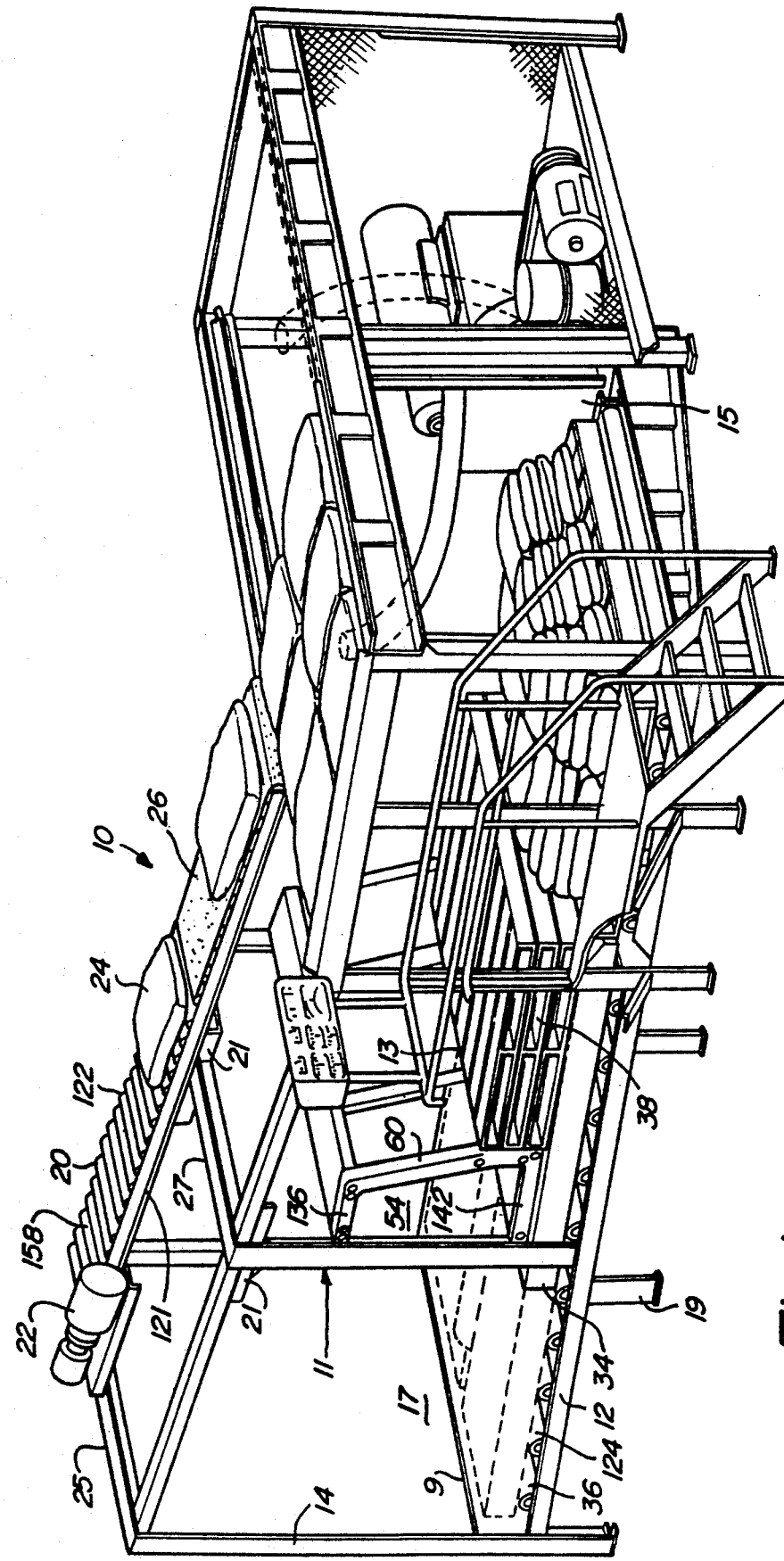

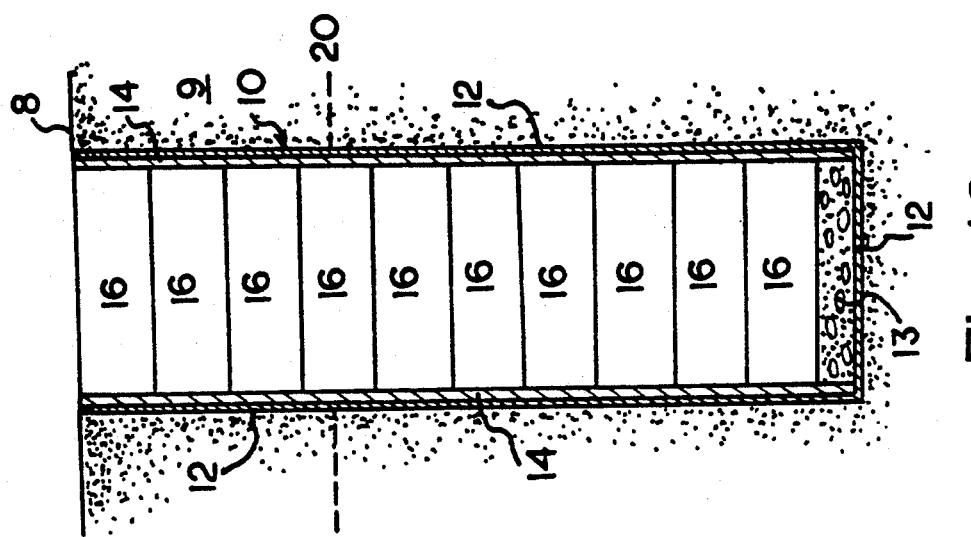
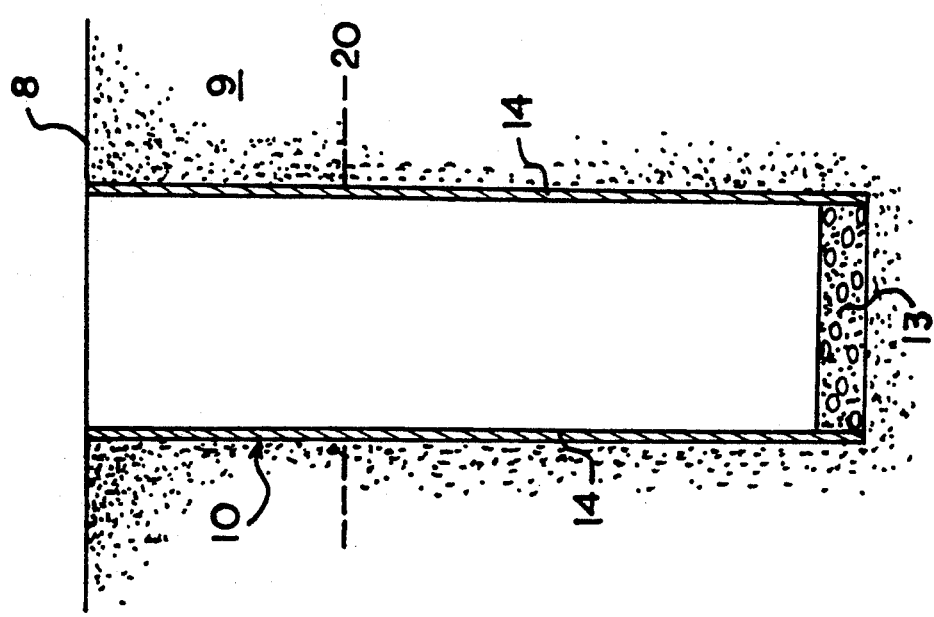

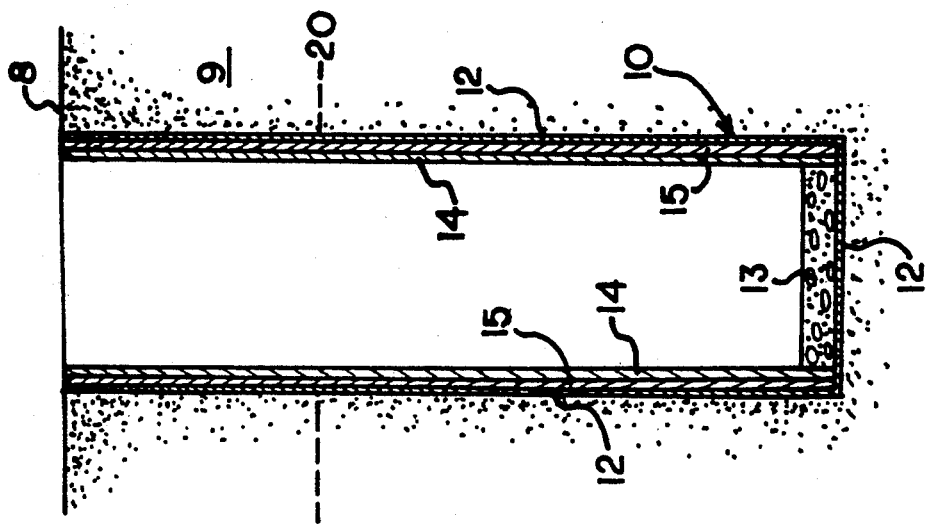
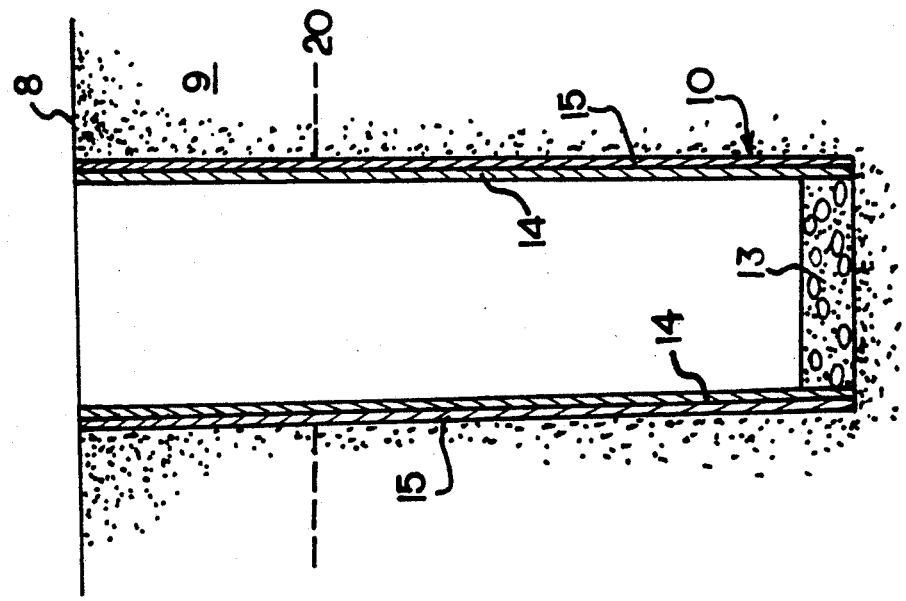

5,261,766

VERTICAL BORE HOLE SYSTEM AND METHOD FOR WASTE STORAGE AND ENERGY RECOVERY

This is a continuation-in-part of Ser. No. 757,048, filed Sep. 9, 1991, now abandoned.

This invention relates to a method of construction of municipal sanitary landfills. In particular it relates to at least one vertical bore hole in natural earth, which is designed to comply with current environmental laws and regulations, such as those existing in Canada and the United States.

Although the invention will be described and referred to primarily as it relates to at least one vertical bore hole in natural earth in municipal sanitary landfills, it will be understood that the principles of this invention are equally applicable to related waste systems and accordingly, it will be understood that the invention is not limited to such vertical bore holes in natural earth.

BACKGROUND AND PRIOR ART

The human race has generated increasing volumes of waste per capita since prehistory. Archeology is mainly excavation of waste dumps. The earliest known settlements are buried in their own waste.

The current generation of waste, leaving aside hazardous, toxic, radioactive and industrial waste.. pollution and other effects, is already well past the crisis level. A major problem is disposal of solid waste at the municipal level. This solid waste includes residential, institutional, commercial and industrial solid waste.

The major component of waste in North America is residential solid waste. At present municipal solid waste (solid waste directly disposed of by municipal authorities) is mostly residential solid waste.

The volume of residential solid waste has grown with increasing population, increasing urbanization, and increasing consumption. The answer to solid waste disposal has been municipal waste disposal sites evolving into sanitary landfills. At present residential solid waste is being generated at a level approximating 1 ton (2,000 lbs per capita, annually, in North America, or approximately 2 cubic meters, (70 cubic feet). In most urban environments solid waste disposal is already a major problem.

Elsewhere even though solid waste production is less per capita, the population is generally denser, consequently municipal solid waste disposal is similarly a major problem.

The growth of world population and urbanization, (estimated to reach 10 billion and 50% of population, respectively by 2050) will exacerbate the solid waste disposal problem. The inevitable proliferation of conurbations of 5 million plus, will propel it into crisis. Conurbations of such size have already lost control of their solid waste disposal.

Even were sufficient land available for sanitary landfills, which is not the case, even in relatively unpopulated North America, there are already environmental problems, which are inevitably escalating to environmental crisis.

In conventional current landfill, the soil is excavated, typically to a lesser depth than the permanent groundwater table. A compacted layer or stratum of soil forms the bottom of the landfill, which is covered with a impermeable plastic liner, or a geotextile, to allow contaminated liquid leachates access to removal points rather than escaping into the groundwater. Even when geotextiles are used excavation is not generally permitted below 5 feet (1.5 meters) above the permanent groundwater table. Every form of solid waste is then deposited to a compacted "lift" typically 6 to 10 feet deep forming a horizontal cell. A shallow stratum of compacted soil.. typically 1 to 3 feet deep is then deposited on the waste materials and the process repeated. The resulting mass of landfill generally rises above original ground level, in some cases up to 150 feet high, forming a "mountain" of waste. Some of these are gigantic, the Fresh Kills site adjacent New York City, being large enough to be visible from the Moon. There are thousands of similar mountains of waste throughout North America.

In practice the landfills are sources of pollution and contamination. Older landfills may not have an impermeable liner, or leachate removal system, and their leachates contaminate the soil and groundwater. Newer landfills are not supposed to allow leachates to escape, however geotextiles, liners and geomembranes are nearly always ruptured to some extent by hydrostatic pressure, man made events or natural phenomena. This allows leachate to contaminate the groundwater to an increasing degree. The air is contaminated downwind of the landfills for considerable distances, similarly neighboring soil and water are contaminated, by airborne and waterborne waste, surface runoff and subsurface groundwater migration. A landfill in use is often infested with birds, rodents and litter. Besides this the landfill site itself is contaminated for at least several decades, and generates quantities of fermentation gas, mainly methane and carbon dioxide. As the contents of landfills are variable and unknown it is difficult to take counter measures to prevent pollution and contamination of the local environment. It is also difficult to predict the long term effects of such contamination and pollution. Consequently the interim use of former landfill sites is restricted to parks, recreation areas, etc., for many years after the landfill decommissioning. This is a gross misuse of valuable natural resources.

PRIOR LANDFILL ART

U.S. Pat. No. 2,164,536 issued Jul. 4, 1939, to McCarthy. U.S. Pat. No. 3,675,428 issued Jul. 11, 1972 to Watts, U.S. Pat. No. 3,835,652 issued Sep. 17, 1974 to Hignite, U.S. Pat. No. 4,026,355, issued May 31, 1977, to Johnson et al., U.S. Pat. No. 4,323,367 issued Apr. 6, 1982 to Ghosh, U.S. Pat. No. 4,469,176 issued Sep. 4, 1984 to Zison et al., U.S. Pat. No. 4,518,399 issued May 21, 1985 to Croskell et al., U.S. Pat. No. 4,643,111 issued Feb. 17, 1987 to Jones, U.S. Pat. No. 4,705,429 issued Nov. 10, 1987 to Natale, U.S. Pt. No. 4,877,353 issued Oct. 31, 1989 to Wisotsky, Sr., U.S. Pat. No. 5,000,617 issued Mar. 19, 1991 to Eggert et al., U.S. Pat. No. 5,000,618 issued Mar. 19, 1991 to Greenley., teach details of waste disposal methods, as do Canadian Patents 1,188,525, issued Jun. 11, 1985 to Matich et al., 1,253,702, issued May 9, 1989 to Sagefors, and European Patents 278,557 published Aug. 17, 1988 to van de Velde et al., and 294,656 published Dec. 14, 1988 to Wunderatzke, and Japanese Patent 60-112908 (A) published Jun. 19, 1965, Kitagawa.

Hignite teaches to form uncased or unlined bore holes in firm soil (temporary casings are specifically excluded col. 2, line 51) above the water table (col. 2, lines 45 to 47, and claim 1, line 4). No protection against soil or water contamination is indicated, which is now environmentally unacceptable in both Canada and USA.

Firm soil conditions (clay, etc.) alone are rarely encountered, Typically in most of North America surficial soil strata include clay, silt, sand, gravel, glacial till, glacial clay, siltstone, sandstone, limestone, etc., and temporary casing is required to excavate in these strata. Further the groundwater table is often only 2 or 3 feet below the surface. To store 44,000 cubic yards of landfill per acre, as alleged would require 50 foot deep, 10 foot diameter holes spaced 2 feet apart. Due to normal variable soil conditions and ground water table elevation, this configuration can not be constructed with 2 feet 0 inches spacing. Hignite is far too restricted by water table depth and soil conditions to store large amounts of waste material, and does not provide any environmental safeguards against water and soil contamination. The assembly of dump tray and funnel member also does not provide any environmental protection, or assistance in drilling as it is designed for use during filling the hole.

Watts teaches to form and fill bore holes similar to Hignite, using a machine consisting of an external casing with an integral internal compact garbage within the hole. The auger is mounted within and fixed to the casing by a thrust bearing. The casing also supports a ring gear and reduction motors to rotate the auger, plus any excavated material. The auger which is smaller than the casing allegedly bores into the ground carrying the larger casing thereafter. Excavated material is allegedly carried up the auger flights to a discharge port in the casing. When auger and casing are at full depth waste is then introduced through another port and the auger rotation reversed allegedly compacting the waste. As this occurs the auger rises and draws the casing from the hole. In applicant's considerable experience a larger casing will not follow a smaller hole, auger flights do not of themselves convey excavated material to the surface, nor compact it back in the hole on reversal, there is no reason to believe the device operational. The device resembles a vertical grain auger, the horizontal version of which frequently plugs. The objects of the invention are distinct from those of instant application.

Van de Velde teaches to drive hollow piles into contaminated earth, close the bottom of the piles and remove the piles containing the earth, and transfer them to a safe site for treatment. The piles are driven by known methods, driving, vibrating or hydraulic pressing, circular, rectangular, or polygonal piles, preferably page 2, col 2, lines 51 to 52, of cross sectional area 4 and 9 sq. meters (42.3 and 95.2 sq. ft.) and from FIG. 7 about 15 meters (50 ft.) deep giving dead weights of 166 and 360 tons not including frictional resistance which would easily double the crane capacity required to 320 and 720 tons. Such portable cranes are rarely available. Transporting such weights would also constitute an enormous problem. The object of the invention is to isolate, treat or remove strongly polluted material present in or on the soil (page 2, col. 1, lines 36 to 40), which is distinct from the objects of instant application.

Gosh teaches to treat solid organic waste in landfills to produce methane gas production. He basically pumps leachates obtained from the bottom of a lined conventional landfill and ferments them externally. Allowance is made for collection of internally generated methane, but the complex system and method are primarily directed to external generation of methane, using acid and methane digesters, countercurrent enhanced supernatant flow, and extraction of leachate generated within the land fill. The objects of Ghosh (col. 3, lines 5 to 22) are to provide a process of improved gas production from landfills of solid organic waste, itself defined as paper products, wood, textiles, rags, food and garden waste, referred to as 'total cellulosics' (sic) excluding metallics, glass, ceramics, dirt, ash, rocks, plastics, rubber, leather, and bulky materials referred to as 'total non-cellulosics' (sic) (col. 3, line 65 to col. 4, line 13). This does not segregate the relatively recyclable cellulosic newsprint and paper products, not of themselves a severe problem from the food and garden waste (or kitchen and yard waste), which is the major source of leachates causing air, soil, and water contamination. The other objects of Ghosh are to reduce fire, explosion and pollution hazards from methane around landfills, to increase methane content of gases produced by anaerobic digestion of solid organic waste landfills, to provide a process suitable for landfills of all sizes, to provide a method of disposing of municipal solid waste, sewage, and sludge within a sealed landfill. The objects of instant application are distinct from Ghosh.

To applicant's extensive knowledge none of these patents has been utilized in the field of waste disposal, and will not be utilized because of current and pending environmental regulations.

HOLE DRILLING PRIOR ART

Hole drilling technology varies with hole diameter, depth, soil conditions and equipment used.

Small holes may be excavated to virtually any depth, by rotating tricone bits attached to a hollow pipe driven by a kelly bar from the surface. Simultaneously drilling mud is pumped down the pipe to carry away the drilled tailings, well known in the oil well art. Typically this technology applies to holes of 6 to 10 inch (15 to 25 cm) diameter, sometimes 12 inch (30 cm) diameter.

Alternatively smaller holes may be excavated by augers, these are typically continuous single flight augers, with a single cutting edge. More rarely double flight augers with a double cutting edge may be used. Such augers typically vary in diameter from 4 inch to 30 inch, exceptionally upward to 36 inch, more rarely to 48 inch, Holes as deep as 30 to 50 feet may be excavated using a series of joined augers having five or six flights apiece, under ideal soil conditions (cohesive clay). The system is limited by the large torque that must be applied, caused by the frictional resistance of the soil being excavated and the weight of soil to be removed. For example a 48 inch diameter hole, 50 feet deep contains approximately 50 short tons of soil, which is way beyond the usual limits of this technology. Typically available standard drill rigs up to 50,000 footpounds torque also effectively limit the practical application of this technology, which is widely known.

Larger holes require different technology, which is limited to a very small number of very specialized engineering and drilling firms, mainly located in North America. Much of the information in this field is acquired by hands on practice and is not readily accessible. It is a specialized complicated and costly field, which is not widely publicized in the literature, because each site requires different equipment. The general principles are known to manufacturers, distributors, designers and operators of the equipment. Equipment available for this work is capable of producing up to 500,000 foot-pounds of torque. The augers used are individually designed to suit specific applicable soil conditions, as a result there are substantial differences between individual auger systems.

Larger holes up to about 8 foot are drilled in a single operation in normal soil conditions using a heavy duty double flight auger with a double cutting edge, approximately 5 to 6 feet long. The hole is drilled to depth up to approximately 100 feet through cohesive soils, including clay, silted clay, glacial till, mudstone and shale, and similar soil, as those skilled in the art would be aware. The auger is drilled its length down into the soil, then is withdrawn from the hole and the tailings removed. The process is repeated until depth is reached. A single flight cutting single edge auger is less efficient for this purpose, as the single edge produces eccentric torque on one side, causing the hole to drift off true verticality. The double edge double flight auger produces uniform and vertical drilling, except where obstructions occur.

Holes from about 8 to about 30 foot diameter are excavated in a two stage operation. First a smaller pilot or guide hole, typically about 6 foot to about 8 foot diameter is excavated in normal soil conditions using a heavy duty double cutting edge double flight auger, approximately 5 to 6 feet long. The hole is drilled to depth up to about 100 feet through cohesive soils. The auger is drilled its length down into the soil, then auger and tailings are withdrawn, and the tailings removed, the process is repeated until depth is reached.

The second stage consists of using the smaller pilot or guide hole to guide a custom designed heavy duty double flight double cutting edge auger. The auger has a bottom guide, which fits into the smaller pilot hole, the cutting edges extend outward from the pilot to the planned diameter of the hole. This auger is typically 5 to 6 feet long. This cuts the hole to the required diameter and depth in auger length increments.

An alternative auger system may be used in the configuration of a drilling bucket having a single or double cutting edge fixed in a slot to the otherwise closed bucket bottom, which may be hinged.

The excavation may also under some but not all conditions be completed within a coffer dam of driven sheet piling, or other types of shoring up to about 100 feet deep. A crane operated hammer grab is continuously dropped from the surface to fill it with excavated material, which is hoisted to the surface and removed. The final configuration of the excavation at the surface controls the shape of the shaft.

Cohesive soils are ideal conditions. Frequently the drilling is undertaken in areas of rock (igneous rock such as granite, harder shales, limestone, or sandstone for example). In this case a core barrel of the desired diameter of the final hole, typically about 3 to about 30 foot is used rotated by a kelly bar, driving the core barrel through a top cross bracing. The core barrel has a bottom ring of downward and slightly outwardly inclined cutting teeth. There is a helical retaining ring interior of the barrel, which retains the internal core of cut rock. Large diameter core barrels are not usually commercially available for rock drilling, but are custom made to suit the drilling conditions.

Another problem is excessive groundwater, for example from a perched water table, which can collapse the already drilled hole. This is typically the case when the soil is water bearing silt, sand or gravel. In this case the hole is drilled to the depth where problems are noted. Then a casing usually of ½ to 1 inch steel, although sometimes 1 to 2 inches at the top expanding to 3 inches between inner and outer teeth edges, coupled like drill stem coupling, if required by threading and rubber gasket, is utilized. The outer casing diameter is slightly smaller than the drilled hole, and has a length to complete the planned hole, from the surface, optionally the casing has bottom teeth. The casing is then slid down until it contacts the bottom of the predrilled hole, and a heavy duty large capacity vibrohammer is used to vibrate the casing down through the soil to the desired depth. The soil within the casing is then generally removed by a heavy duty double flight double cutting edge auger, or by another appropriate auger. The auger used has external diameter slightly less than the internal casing diameter. The casing is then retrieved using a vibrohammer. Again this clearly indicates that Hignite teachings using conventional equipment cannot extend his excavations below the water table or in soil conditions that develop sloughing such as is generally encountered.

A principal object of the invention is to construct and provide an environmentally safe, acceptable, and efficient method of construction of temporary or permanent landfill for the storage of municipal solid waste, particularly solid organic wastes other than cellulosics, below natural grade, and the permanent natural groundwater table, including at least one vertical bore hole for waste storage and treatment. A further object is the production of methane gas as an alternate or secondary energy source. A further object is the capture of methane gas, reducing one of the more serious greenhouse gas threats to the ozone layer. A further object is the capture and reduction of toxic and other leachates thereby eliminating pollution and contamination of soil, surface water, and underground water. A further object is the production of soil nutrients as compost usable as fertilizer and the like. A further object is to construct and provide a permanent landfill site which can be reused as a waste disposal site after the compost has been removed. A further object is to provide efficient and inexpensive rehabilitation of decommissioned landfill sites no longer required. A further object is to provide an esthetically acceptable landfill site, operable in conjunction with a recycling center, etc. A subsidiary object is to seal the bore hole from the surrounding soil in a watertight and gastight fashion. A further subsidiary object is to extend the bore hole into and significantly below the groundwater table. A further subsidiary object is to provide the bore hole with a rigid structural liner or lining. A further subsidiary object is to protect the environment by providing underground storage facilities. Other objects will be apparent to those skilled in the art from the following specification, appended claims and accompanying drawings.

DESCRIPTION OF THE INVENTION

In one broad aspect the invention is directed to vertical cylindrical bore hole means for waste storage excavated in naturally occurring earth having side and base wall means, and preformed impermeable liner means for the side and base wall means of the bore hole means and distinct internal side casing means within the preformed impermeable liner means, the impermeable liner means and internal side casing means together providing gastight and watertight sealing means between the bore hole means and the naturally occurring earth conditions. Usually the bore hole means extends significantly below the natural groundwater table. Base plug means may be present within the impermeable liner means, abutting the base wall means. A grout layer means may be present external the side casing means and or internal the impermeable liner means. The internal casing means may be formed of interlocking preformed sections. The internal casing means may be formed to include grout layer means. The impermeable liner means, internal casing means, and grout layer means preferably abut each other; their total thickness is typically 1 to 4 inches thick, although as would be realized by those skilled in the art, substantial variation may be required according to circumstance.

Typically the bore hole means is a vertical cylindrical excavation of about 2 to about 50 feet diameter, and depth about 6 to about 200 feet in natural earth. Conveniently the bore hole is about 2 to about 30 feet in diameter. More usually such bore holes are up to about 110 feet deep, sometimes about 130 feet deep, and from about 8 to about 30 feet across. Waste is stored in the completed bore hole, which may be toxic waste, or compacted waste, which may be organic. The waste is enclosed within the bore hole by impermeable liner means. The bore hole when used is typically sealed at the upper end by compacted soil means. In theory the bore hole may be lined with an impermeable liner means alone to prevent or eliminate percolation of its contents into the groundwater. In practice when the bore hole extends below the groundwater table, the impermeable liner means alone is, usually insufficient, and a more rigid structure must be supplied either instead of the impermeable liner means or as well as the impermeable liner means. The natural groundwater table in much of North America lies from 2 to 80 feet below ground level, generally 8 to 12 feet, so nearly any bore hole will penetrate the groundwater table. When the waste is toxic the impermeable liner means should preferably also be chemically inert. The impermeable liner means may be concrete, steel, plastic derivative, or ceramic material, or formed from a suitable grout, as would be known to those skilled in the art. The formed bore hole is then filled with selected waste materials. Waste materials are increasingly being sorted for recycling. Most preferably they can also be sorted for disposal. All sorts of figures for waste are quoted, which vary widely it is fairly certain cellulosics, including newsprint and related paper products (telephone directories, cardboard, paper wrappings, etc.) form a large part of the volume of municipal residential solid waste, Steps are increasingly being taken to recycle these cellulosics. It is proposed to separate solid organic waste other than cellulosics from the residue of metals, wood, glass, plastic, construction and demolition, ceramic and miscellaneous wastes, which will also be sorted. Preferably each different type of waste will be either recycled directly or stored separately either on the surface or in bore holes.

The bore hole as required by local conditions may receive bottom lift of compacted soil 1 to 3 feet deep. Waste is then deposited, preferably in 20 to 30 feet lifts in the bore hole, which are then compacted to reduce volume. Again as required by local conditions a sandwich lift of compacted soil 1 to 3 feet deep may be deposited within the bore hole to produce 1 cell of the unit. The process is repeated until the compacted waste fills the bore hole to within 4 to 6 feet of the surface. To complete the last cell a lift of sail is compacted within the top of the bore hole, until original grade level is reached. Similar bore holes may be constructed following a grid system.

Using this system properly calculation has shown, will enable storage an a square site of 1 acre, of some 130,000 cubic meters of compacted waste. A conventional landfill 136 feet thick, 60 feet below grade and 76 feet above grade, will store less material some 100,000 cubic meters. This does not include sorting or recycling the waste. Additional advantages are all storage is below original grade level, avoiding the mountain of rotting waste. Soil and air pollution are eliminated, when an impermeable liner is utilized. Litter, birds and rodents are eliminated. The site can be planned to accommodate the ongoing volume of waste products in the locality. Each bore hole is confined to a limited area, allows safe construction practices to be established and enforced. The variation in vertical bore hole size, allows considerable variation in bore hole capacity to allow for different waste volume needs. Bore holes can be utilized for temporary storage of hazardous, toxic or corrosive, industrial wastes. The bore hole system can be constructed under all weather conditions.

As an alternative (or in addition to) providing an impermeable lining or liner to the bore holes) as may be required by specific conditions or regulations, a slurry wall can be constructed around the landfill perimeter. The slurry wall is constructed by excavating a trench from 0.5 to 4 feet wide is excavated to below maximum depth of the landfill bite, preferably footed in solid rock and filled with bentonite or other material that prevents migration of leachates, etc., into the surrounding area. This is particularly effective in preventing the migration of hazardous chemicals such as PCBS.

In another aspect the invention is directed to an improved method of construction of vertical cylindrical bore means for waste storage in naturally occurring earth. It is known to excavate cylindrical bore hole means, having side and base wall means to the natural ground water table, then to vibrate temporary external casing means to required depth, excavating soil within the external casing means, and further to vibrate the temporary external casing means out of the bore hole means. The improvement provides comprising the steps of (a) inserting preformed impermeable liner means within the external casing means, (b) providing internal casing means within the preformed impermeable liner means, to provide gastight and watertight sealing means between the bore hole means the naturally occurring earth. Preferably (c) base plug means within the preformed impermeable liner means abutting the base wall means are provided. Preferably (d) grout layer means between the internal casing means and the preformed impermeable liner means are provided. Preferably (e) the internal casing means may be formed of grout layer means. Preferably (f) the preferred impermeable liner means is custom made to fit the bore hole means on jig means (g) transported to the bore hole means and (h) inserted within the bore hole means. Preferably (i) the internal casing means is formed from interlocking preformed sections.

The waste is preferably sorted and stored according to type. Non-cellulosic organic solid waste, is preferably segregated then deposited separately in designated bore holes. This organic solid waste is generally residential kitchen and food waste, and residential yard waste, also there is industrial waste of similar composition. It can be fermented to methane.

In a further broad aspect the invention is directed to an improved process of anaerobic fermentation of non-cellulosic organic solid waste. It is known to allowing the waste to ferment in the absence of air, and to withdraw gaseous fermentation products. The improvement comprises (a) compacting segregated non-cellulosic organic solid waste within bore hole means sealed from naturally occurring earth by watertight and gastight liner means, (b) allowing the fermentation to terminate naturally (c) removing the fermented organic solid waste as compost (d) repeating steps (a) to (d). Preferably the step is taken of (e) addition of anaerobic methane generating organisms to the compacted organic solid waste. Such organisms are well known see for example Ghosh, U.S. Pat. No. 4,323,367 and references therein. Additionally the steps are taken of (f) coring the compacted organic waste to provide core hole means and (g) providing gas removal conduit means within the core means.

Bore holes of diameter about 6 to about 30 feet, and depth about 8 to about 200 feet, are contemplated for this process. A central hole preferably cored, after compaction of the waste to form a central core hole means preferably of 16 to 30 inch diameter, which is utilized as would be known by those skilled in the art as gas removal conduit means. For instance a perforated sleeve, or a column of porous material such as pea gravel, gravel, sand, and the like, or a perforated sleeve containing porous material, or other known conventional gas removal means are placed in the central core hole. The gas removal means is connected to a conventional gas collection system by tube means. The solid organic waste first ferments aerobically consuming oxygen within the sealed liner, as in existing landfills. When the oxygen is consumed, anaerobic fermentation begins, if necessary an activated culture of anaerobic micro-organisms can be injected into the top of each vertical bore hole. After removal of the compost the bore hole is refilled with compacted segregated non-cellulosic organic waste.

The use of fermentation bore holes effectively harnesses methane production, and eliminates it as a pollutant. It further reduces the amount of waste to be stored. It is believed that about half of residential waste by weight is such fermentable organic waste. This gives an estimate of methane generated per capita in North America of 6500 cubic feet, and compost generated per capita of about 1000 lbs.

BRIEF DESCRIPTION OF THE DRAWINGS

Preferred embodiments are indicated in the drawings where:

FIG. 1 shows a side sectional view of a bore hole of the invention as initially prepared;

FIGS. 2 to 7 show side sectional views of the embodiment of FIG. 1, in further stages of preparation;

FIGS. 9 to 14 show side sectional views of completed embodiments of the invention.

DESCRIPTION OF THE PREFERRED EMBODIMENTS

Figure 4:
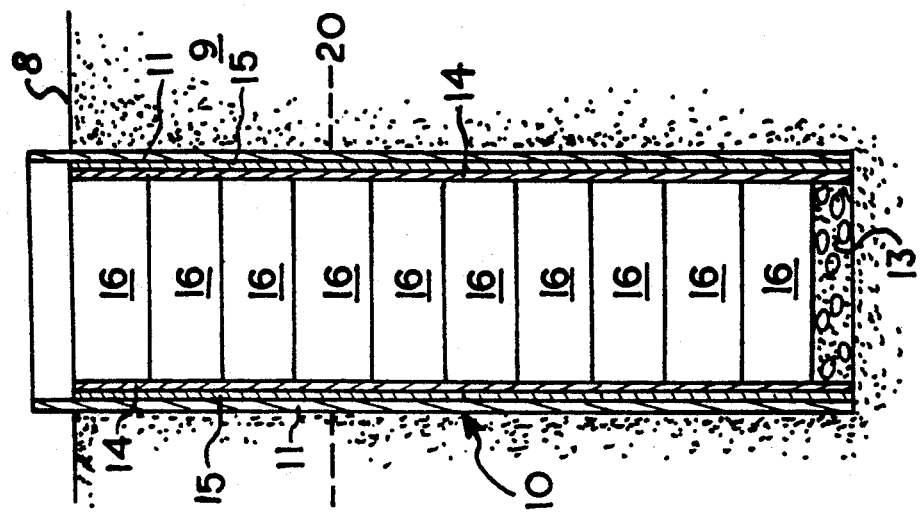

The general description of the invention is now expanded by reference to the drawings, which illustrate preferred embodiments of the invention.

Numeral 10 generally indicates a vertical cylindrical bore hole excavated from original grade level 8 in natural soil 9, by known developed methods. Numeral 20 indicates the natural groundwater table, which varies with locality and time. Generally excavations extending below the natural groundwater table require temporary shoring or casing during construction. This is usually supplied by installing a temporary external shoring or casing, all the way down to the bottom of the excavated hole, to extend and maintain hole configuration to required depth. In FIGS. 1 to 7 the casing is provided by temporary external vibrohammer casing 11, which has been vibrated to the required depth. These bore holes can be typically 2 to 30 feet diameter and 6 to about 190 to 200 feet deep. Standard currently available equipment does not allow excavating bore holes deeper than 190, 195 or 200 feet from the surface, deeper holes are virtually impossible to excavate using available equipment. To applicant's extensive knowledge in this field, readily portable commercially available equipment has not so far been constructed to dig holes deeper than this from the surface. Holes larger than this could be utilized in the invention, but are not normally constructed at present. The holes are typically cylindrical, apart from the fact temporary external vibrohammer casing 11 is conveniently cylindrical, this assists in the ease and economy of construction. Further cylindrical holes have balanced internal stresses of soil cohesion.

The holes are typically constructed by drilling a pilot hole from about 2 to about 6 feet diameter down until it strikes water bearing or incohesive soil. The main bore hole is then drilled to the same elevation. The temporary external vibrohammer casing, which is slightly smaller than the main bore hole, is then inserted and vibrated down to the final depth. Occasionally soil cohesion and the like, as would be understood by those skilled in the art, affect the vibrohammer casing sufficiently that the soil within the casing has to be excavated while the casing is being vibrated to final depth. In some instances geotechnical considerations as would be known to those skilled in the art, may require rotation of the large bore casing within the hole as it drilled and/or vibrated. In this case the bottom of the temporary external vibrohammer casing is designed with a special toothed configuration, as would be known to those skilled in the art.

When the temporary external vibrohammer casing has reached final depth any remaining soil within the bore hole and casing is excavated by an auger of diameter slightly smaller than the internal dimensions of the casing.

An impermeable liner is then formed to conform to the internal dimensions of the temporary external vibrohammer casing 11 within excavated hole 10. The impermeable liner is formed as a tube around a jig or frame work slightly smaller in size than the internal dimensions of temporary casing 11. Impermeable liner tube 12 is fabricated by sealing overlapping sections of suitable material by methods known to those skilled in the art. It is then removed to the hole excavation site and lowered into it on a frame work or casing and weighted at the lower end. The result is shown in FIG. 2, which may be used as is, following removal of the external casing 11. The bottom of tube 12 is sealed with a quick setting grout or concrete or the like plug 13, which is introduced through a tremie, a long chute with a bottom valve allowing the grout, concrete or the like to be deposited reducing impact on the impermeable liner at the bottom of the hole.

In special cases it may be necessary to insert concrete permanent liners or other internal casings within the hole with or without a impermeable liner.

Figure 3:
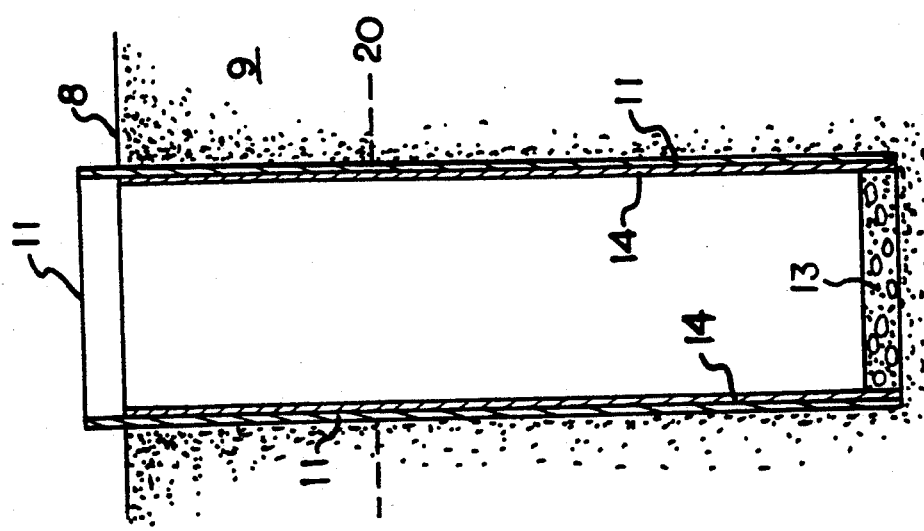
Figure 5:
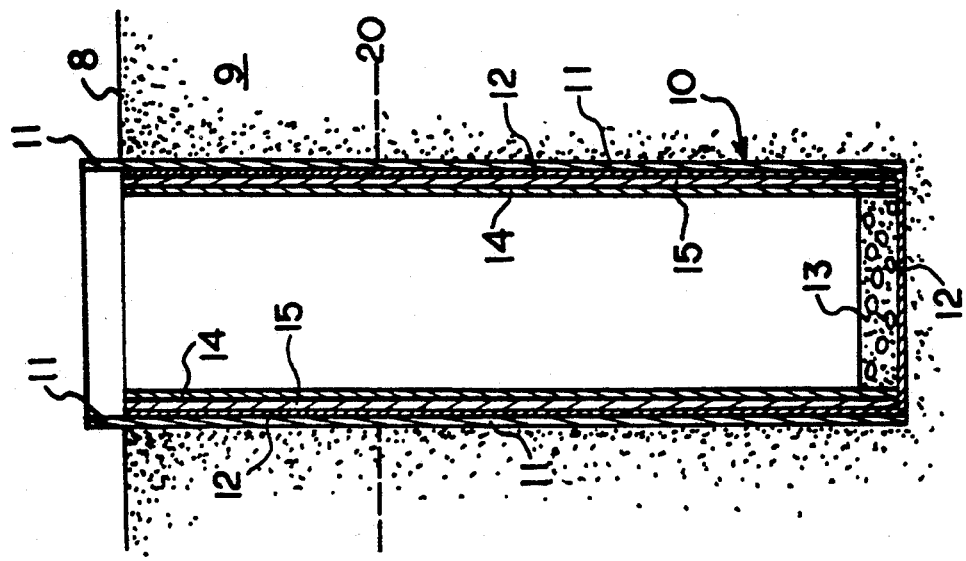
Figure 6:
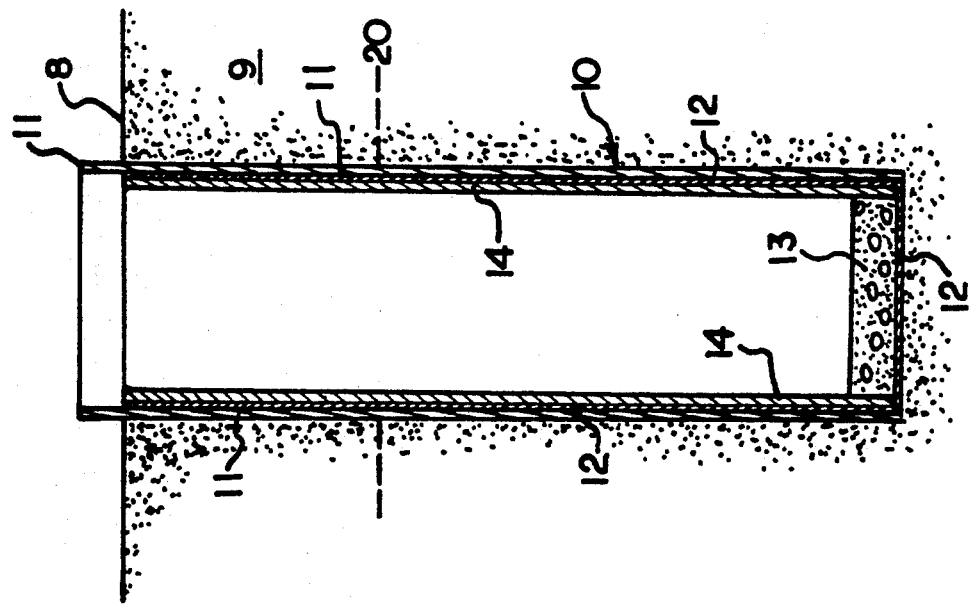
Figure 7:
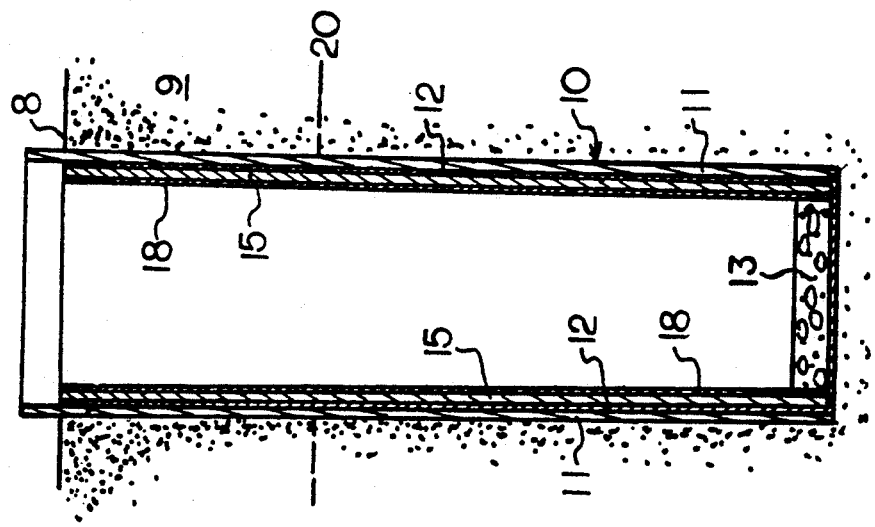

In FIG. 3 a permanent internal casing or pipe 14 may be inserted within the external temporary steel casing 11, without a impermeable liner being present, again the bottom of the hole is sealed with grout, concrete or the like plug 13. The internal casing or pipe may be a cylindrical casing or corrugated pipe formed from suitable concrete, plastic, steel, ceramics, metals suitable for construction purposes, ferroconcrete, and selected from materials which either do not corrode, or very little under the conditions. The casing may be made from preformed sections especially concrete and lowered into hole 10 with special interlocking joints for coupling and sealing. Such joints are used in excavations such as caissons, where high water pressure requires that the caisson excavation be sealed, as known by those skilled in the art. The joints are preferably grouted, and must be totally watertight. External grouting 15 may be applied between inner permanent casing 14 and external temporary casing 11 as in FIG. 4, here permanent inner casing 14 is formed of preformed sections 16. Impermeable liner 12 may be present as in FIG. 5, with inner permanent casing 14 inside it, optionally external grouting 15 may be applied between inner permanent casing 14 and impermeable liner 12 as in FIG. 6. A specially preferred version is shown in FIG. 7, where a temporary inner casing 18 is emplaced within impermeable liner 12 and external grouting 15 introduced allowed to set then both inner casing 16 and external casing 11 are removed.

Figure 8:
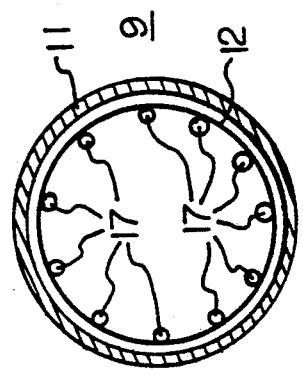
FIG. 8 shows a plan sectional view of a bore hole of the invention containing a grouting impermeable liner.

External grouting 15 may be selected from suitable materials known to those skilled in the art, such as plastics and cements. When a impermeable liner is present they may be introduced by internal tubes 17 attached to the inside of impermeable liner 12, as shown in FIG. 8, spaced 2 to 4 feet apart around the internal perimeter of the impermeable liner.

Figure 13:
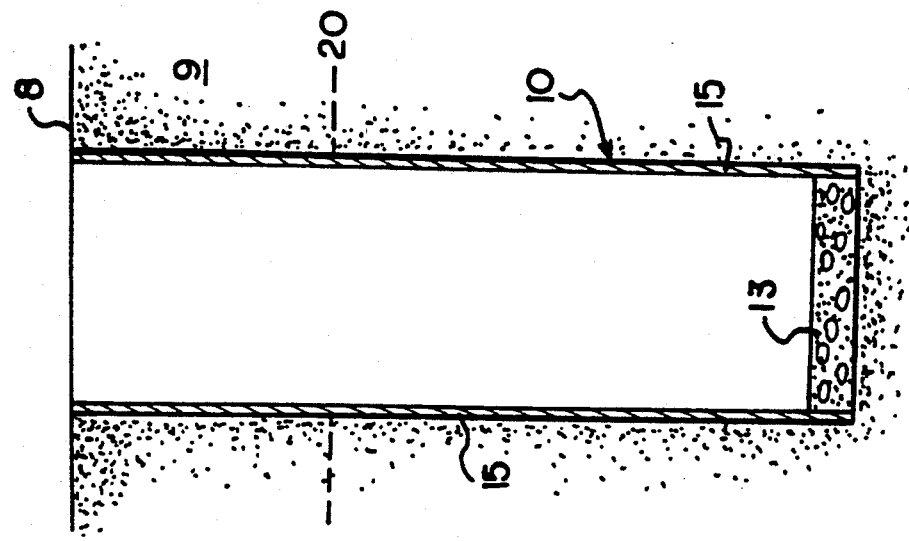
Figure 14:
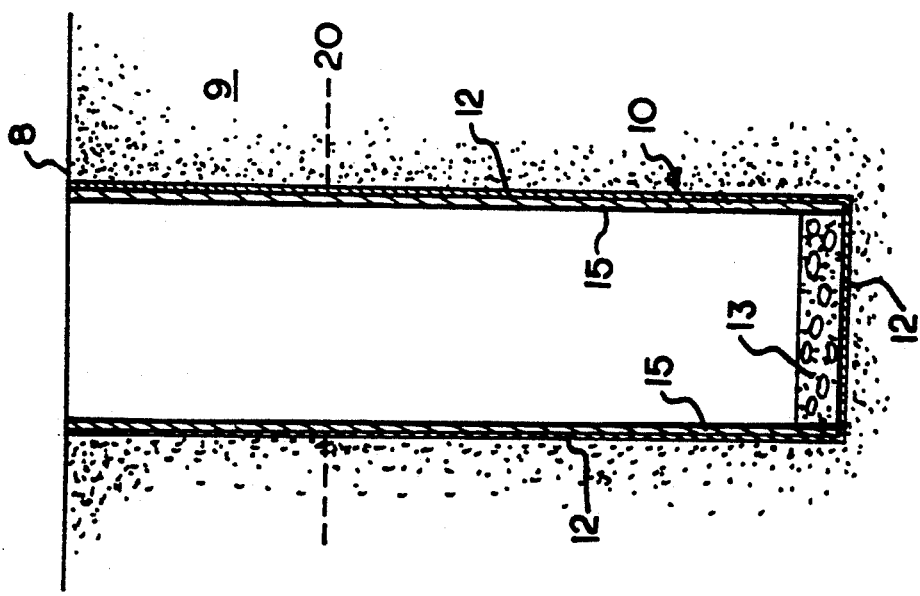

The constructed bore holes are shown ready for use in FIGS. 10 to 14. FIG. 9 shows inner casing 14, sealed at the bottom by concrete plug 13. FIG. 10 shows inner casing 14, sealed at the bottom by concrete plug 13, inner casing 14 is composed of cylindrical preformed interlocking sections 16, impermeable liner 12 lines hole 10 outside plug 13 and inner casing 14. FIG. 11 shows inner casing 14, sealed at the bottom by concrete plug 13, grout 15 laterally surrounds inner casing 14. FIG. 12 shows inner casing 14, sealed at the bottom by concrete plug 13, grout 15 laterally surrounds inner casing 14, impermeable liner 12 lines hole 10 outside plug 13 and grout 15. FIG. 13 shows cylindrical grout 15 forming a casing, sealed at the bottom by concrete plug 13, impermeable liner 12 lines hole 10 outside plug 13 and grout 15. FIG. 14, shows cylindrical grout 15 forming a casing sealed at the bottom by concrete plug 13.

The system envisages separation of solid organic waste other than cellulosics from all other solid waste, for example metal, wood, plastic, newsprint, construction and/or demolition rubble, etc. These other solid wastes can be recycled or stored permanently or temporarily in vertical bore holes 10. Similarly toxic wastes can be stored in vertical bore holes of this system.

As those skilled in the art would realize these preferred illustrated dimensions, details and components can be subjected to substantial variation, modification, change, alteration, and substitution without affecting or modifying the function of the illustrated embodiments.

This invention is not limited to the embodiments described above, and it will be apparent to persons skilled in the art that numerous modifications and variations form part of the present invention insofar as they do not depart from the spirit, nature and scope of the claimed and described invention.

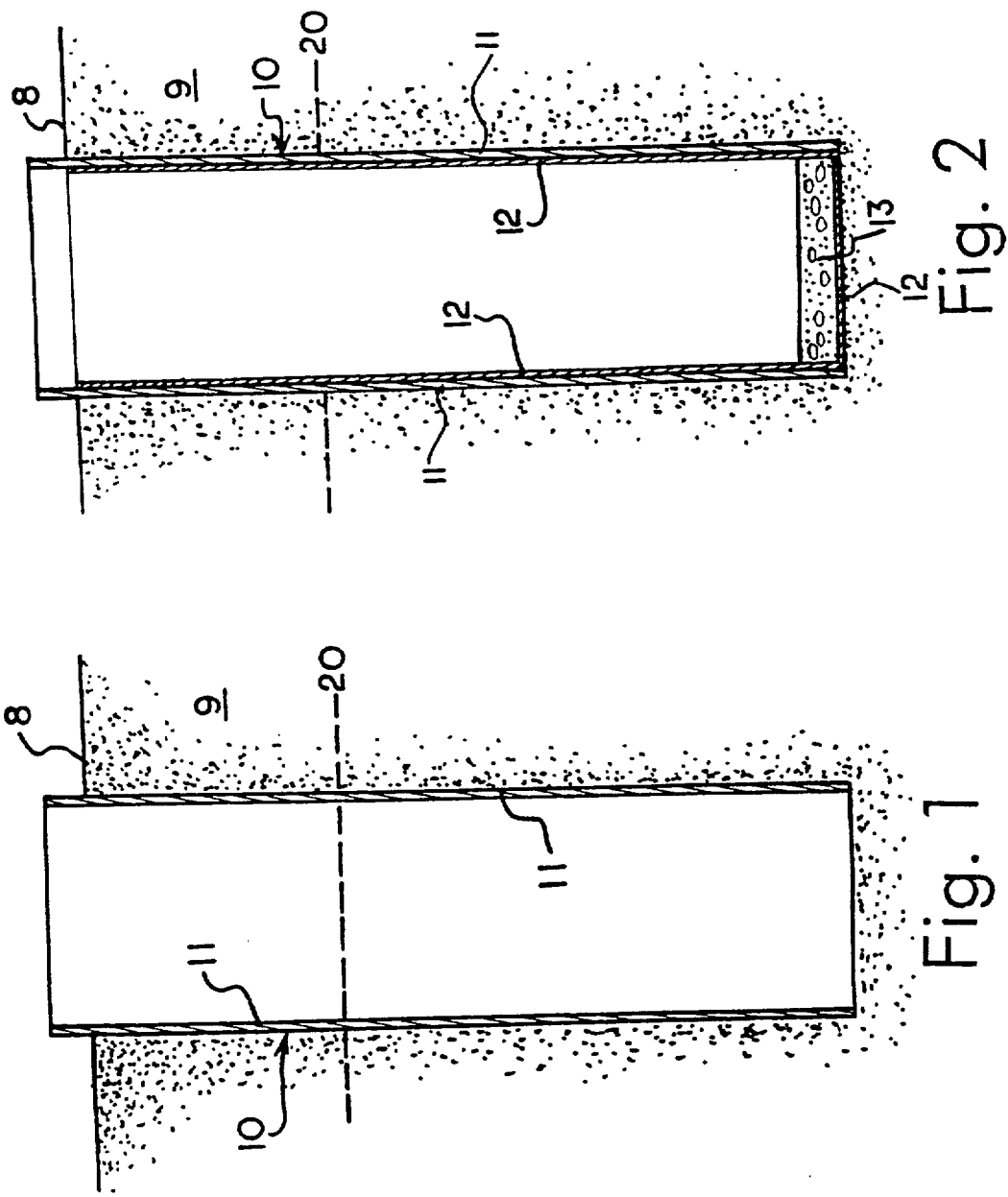

I claim:

1. Vertical cylindrical bore hole means, extending below the natural groundwater table, for waste storage, said bore hole means being excavated in naturally occurring earth having side and base wall means, and preformed impermeable liner means abutting said side and base wall means of said bore hole means, and distinct internal side casing means within said preformed impermeable liner means, said impermeable liner means and internal side casing means together providing gastight and watertight sealing means between said bore hole means and said naturally occurring earth conditions, wherein base plug means are present within said impermeable liner means, abutting said impermeable liner means adjacent said base wall means.

2. Bore hole means of claim 1 additionally comprising grout layer means external said internal side casing means and internal said preformed impermeable liner means.

3. Bore hole means of claim 2 wherein said grout layer means abuts said internal side casing means and said preformed impermeable liner means.

4. Bore hole means of claim 1 wherein said preformed impermeable liner means abuts said internal side casing means.

5. Bore hole means of claim 1, wherein said internal casing means comprises grout layer means.

6. Bore hole means of claim 5, wherein said preformed impermeable liner means abuts said grout layer means.

7. Vertical cylindrical bore hole means, extending below the natural groundwater table, for waste storage, said bore hole means being excavated in naturally occurring each having side and base wall means, and preformed impermeable liner means abutting said side and base wall means of said bore hole means, and distinct internal side casing means formed of interlocking section means within said preformed impermeable liner means, said impermeable liner means and internal side casing means together providing gastight and watertight sealing means between said bore hole means and said naturally occurring earth conditions, wherein base plug means are present within said impermeable liner means, abutting said impermeable liner means adjacent said base wall means.

8. Bore hole means of claim 7 additionally comprising grout layer means external said interlocking section means and internal said preformed impermeable liner means.

9. Bore hole means of claim 8 wherein said grout layer means abuts said interlocking section means and said preformed impermeable liner means.

10. Bore hole means of claim 7 wherein said preformed impermeable liner means abuts said interlocking section means.

11. In a method of construction of vertical cylindrical bore hole means for waste storage in naturally occurring earth, including excavating cylindrical bore hole means, having side and base wall means to the natural ground water table, then vibrating temporary external casing means to required depth, excavating soil within said external casing means, and vibrating said temporary external casing means out of said bore hole means, the improvement comprising the steps of (a) inserting preformed impermeable liner means within said external casing means, and before removal of said external casing means from said bore hole means, and after removal of said external casing means, said impermeable liner means being in abutting relationship with said side and base wall means (b) providing internal casing means within said preformed impermeable liner means, to provide gastight and watertight sealing means between said bore hole means and said naturally occurring earth conditions (c) depositing waste within said internal casing means.

12. A method of claim 11 additionally comprising providing base plug means within said preformed impermeable liner means abutting said base wall means.

13. A method of claim 12, additionally comprising providing grout layer means between said internal casing means and said preformed impermeable liner means.

14. A method of claim 13, additionally comprising providing grout layer means to form said internal casing means.

15. A method of claim 12, wherein said internal casing means is formed from interlocking preformed sections.

16. A method of claim 15 additionally comprising providing grout layer means between said internal casing means and said preformed impermeable liner means.

17. A method of claim 15, wherein said impermeable liner means is custom made to fit said bore hole means on jig means transported to said bore hole means and inserted within said bore hole means.

18. A method of claim 11, wherein said impermeable liner means is custom made to fit said bore hole means on jig means transported to said bore hole means and inserted within said bore hole means.

* * * * *

UNITED STATES PATENT AND TRADEMARK OFFICE
CERTIFICATE OF CORRECTION

PATENT NO. : 5,261,766    Page 1 of 2
DATED : November 16, 1993
INVENTOR(S) : James S. Anderson It is certified that error appears in the above-indentified patent and that said Letters Patent is hereby corrected as shown below:

In the drawings, sheet 1, consisting of Figure 1, should be deleted to be replaced with the sheet of drawings consisting of Figures 1 and 2, as shown on the attached page.

Signed and Sealed this

Second Day of August, 1994

Attest:

BRUCE LEHMAN

Attesting Officer    Commissioner of Patents and Trademarks